(12) United States Patent
Studer

(10) Patent No.: US 6,758,362 B2
(45) Date of Patent: *Jul. 6, 2004

(54) SPECIMEN HOLDERS FOR HYDROUS SPECIMENS AND METHOD OF USING THEM

(75) Inventor: Daniel Studer, Schweiz (CH)

(73) Assignee: Leica AG, Wien (AT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/006,387

(22) Filed: Jan. 13, 1998

(65) Prior Publication Data

US 2002/0108957 A1 Aug. 15, 2002

(30) Foreign Application Priority Data

Jan. 13, 1997 (SE) ................................................ 0053/97

(51) Int. Cl.⁷ .............................................. B65D 88/74
(52) U.S. Cl. ........................ 220/592.01; 62/66; 435/1.3
(58) Field of Search ...................... 220/592.01, 592.28, 220/665, 23.87, FOR 134, FOR 138, FOR 140; 435/1.3, 284.1, 304.1, 297.4; 62/336, 903, 66

(56) References Cited

U.S. PATENT DOCUMENTS

| | | | | |
|---|---|---|---|---|
| 1,576,955 A | * | 3/1926 | Dubraks ...................... 220/592 |
| 3,004,657 A | * | 10/1961 | Hyman ...................... 220/23.87 |
| 3,481,477 A | * | 12/1969 | Farr ............................. 210/359 |
| 3,558,066 A | * | 1/1971 | Alliger ............................ 241/2 |
| 3,677,024 A | * | 7/1972 | Segall ........................... 435/1.3 |
| 3,848,593 A | * | 11/1974 | Bladwin ...................... 604/206 |
| 3,859,051 A | * | 1/1975 | Natelson ....................... 422/64 |
| 3,883,393 A | * | 5/1975 | Knazek et al. .............. 435/400 |
| 4,024,857 A | * | 5/1977 | Blecher et al. .............. 422/102 |
| 4,081,345 A | * | 3/1978 | Tolg et al. ................... 204/405 |
| 4,107,937 A | * | 8/1978 | Chmiel ........................ 435/1.3 |
| 4,152,939 A | * | 5/1979 | Renshaw .................. 73/864.02 |
| 4,184,922 A | * | 1/1980 | Knazek et al. ............ 435/297.4 |
| 4,443,546 A | * | 4/1984 | Stemerman et al. ......... 435/387 |
| 4,454,235 A | * | 6/1984 | Johnson ...................... 436/536 |
| 4,537,860 A | * | 8/1985 | Tolbert et al. .............. 435/401 |
| 4,688,387 A | | 8/1987 | Conaway |
| 4,720,462 A | * | 1/1988 | Rosenson ................ 435/286.6 |
| 4,799,358 A | | 1/1989 | Knopf et al. |
| 5,015,585 A | * | 5/1991 | Robinson .................... 435/401 |
| 5,156,813 A | * | 10/1992 | Calhoun ..................... 422/102 |
| 5,283,170 A | * | 2/1994 | Cassou et al. ............... 435/1.3 |
| 5,334,502 A | * | 8/1994 | Sangha ...................... 435/7.21 |
| 5,935,848 A | * | 8/1999 | Sputtek et al. ........... 435/307.1 |

FOREIGN PATENT DOCUMENTS

| | | | | |
|---|---|---|---|---|
| DE | 1 806 741 | | 6/1969 | |
| EP | 0 275 829 | | 7/1988 | |
| FR | 1376529 | * | 9/1964 | ........ 220/FOR 140 |
| GB | 1 230 120 | | 4/1971 | |
| JP | 1-157051 | * | 6/1989 | |
| WO | WO 9602801 | | 2/1996 | |

OTHER PUBLICATIONS

D. Studer, et al., "Vitrification of articular cartilage by high–pressure freezing", *Journal of Microscopy*, vol. 179, Pt. 3, pp. 321–332, Sep. 1995.

D. Studer, et al., "High Pressure Freezing Comes of Age", *Scanning Microscopy Supplement*, No. 3, pp. 253–269, 1989.

H. Hohenberg, et al., "High–pressure freezing of cell suspensions in cellulose capillary tubes", *Journal of Microscopy*, vol. 175, Pt. 1, pp. 34–43, Jul. 1994.

* cited by examiner

Primary Examiner—Stephen K. Cronin
Assistant Examiner—Joseph C. Merek
(74) Attorney, Agent, or Firm—Foley & Lardner LLP

(57) ABSTRACT

A specimen holder for a hydrous specimen comprising:
  (a) an inner hollow cylinder of a heat conductive material,
  (b) an inner hollow cylinder of a material which can be cut,
  (c) a cylindrical interior space within the inner hollow cylinder for receiving the specimen, and
  (d) the space between the inner hollow cylinder and an inside wall of the outer hollow cylinder being filled by a layer which is liquid at room temperature.

11 Claims, 4 Drawing Sheets

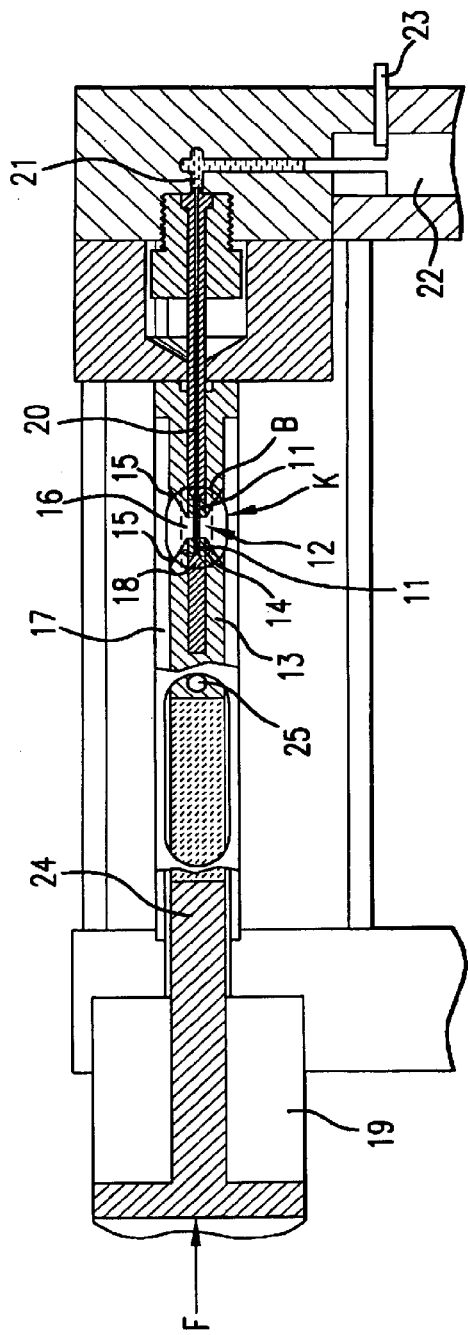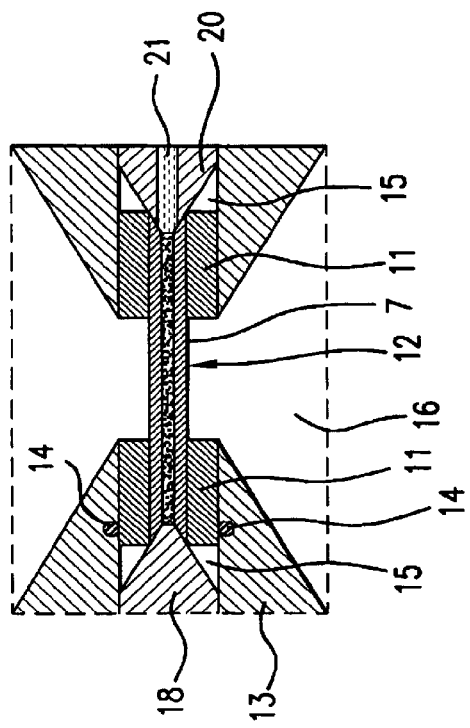
FIG.4A
FIG.4B

SPECIMEN HOLDERS FOR HYDROUS SPECIMENS AND METHOD OF USING THEM

BACKGROUND OF THE INVENTION

1. Field of the Invention

The present invention relates to specimen holders for hydrous specimens, and to methods of using them, and in particular to specimen holders suitable for high-pressure freezing.

2. Description of Related Art

A method of rapidly freezing hydrous specimens under high pressure is generally known, for example, from German Patent DE-B 1 806 741. The advantage of freezing under high pressure as opposed to normal pressure can be explained as follows: if a pressure of about 2000 bar is applied to a specimen during cooling, the cooling rate required for vitrification (no ice crystal formation, no segregations) is reduced by a factor of one hundred, consequently making it possible to vitrify specimens in the form of slices up to a maximum thickness of 200 $\mu$m. It should also be noted that, if there is any ice formation under pressure, the mesh size of the segregation patterns becomes greatly reduced, i.e. hydrous specimens about 200 $\mu$m thick frozen under 2000 bar are optimally preserved ultrastructurally (nanometer range) (STUDER D., MICHEL M., WOHLWEND M., HUNZIKER E. B. and BUSCHMANN M. D., Vitrification of articular cartilage by high-pressure freezing , J. of Microscopy 179 (1295), 312–332). Thus far, the advantage of high-pressure freezing for relatively thick specimens (specimen thickness in the range of around 2 mm) has not been recognized. The reduction in the mesh size of the segregation patterns has the effect that such specimens appear optimally preserved under a light microscope, since segregations in the $\mu$m range are not visible.

The specimen holder described in DE-B 1 806 741 is generally poorly suited for further processing of frozen specimens. It is a tubular, thin-walled container made, for example, of copper which is closed at one end and widened at its upper end in the form of a funnel. The specimen inside this specimen holder is subjected to pressure by a hydraulic system using a pressure transfer fluid, for example, water, and is cooled from outside by spraying on a coolant. The use of this device makes it virtually impossible for the specimens to be further processed after freezing. By applying a predetermined breaking point, it has been possible at least to use a so-called freeze etching technique. With this technique, thin metal impressions are prepared, which can be investigated.

Commercially available high-pressure freezing devices according to the prior art typically operate as follows: they use liquid nitrogen of about −150° C. both as a pressure transfer medium and as a coolant. Its temperature under normal pressure is −196° C.; under 2000 atm, it is solid at this temperature. The apparatus-related disadvantages of such systems, in which liquid nitrogen is used both as a pressure transfer medium and as a coolant, include the following: the machines are relatively large (about 0.8×1.6× 1.5 m$^3$) and heavy (>600 kg). Their use entails a risk of accidents for the operating personnel: the spraying on of over 100 ml of liquid nitrogen under 2000 bar requires relatively large bores in the pressure chamber, which accordingly has to be of a very solid construction. Accidents are known; thus far, no instances of personal injury have occurred, but property damage can run into very high FIGS. (5–20,000 Swiss Francs). The costs of these apparatuses continue to be relatively high, since they have to be produced in small numbers from high-grade materials (150–300,000Swiss Francs).

In such systems, the biological specimens are generally located in two thin-walled metal half-shells (so-called aluminum sandwich: about 3 mm outside diameter, inside diameter about 2 mm, with a variable cavity thickness of 100–600 $\mu$m), which are securely clamped between two steel plates. These plates are securely bolted to a solid steel impeller (specimen holder). This specimen holder is introduced with the specimen into a high pressure chamber and arrested by a solid transverse bolt. The high pressure chamber is sealed by an O-ring on the specimen holder.

The freezing cycle in the above-described systems typically proceeds as follows: to coordinate the pressure increase and cooling, the high pressure chamber is initially filled for about 30 ms with ethanol, in order to permit the correct correlation of the pressure increase and the cooling. Then, about 100–160 ml of cold liquid nitrogen is passed by means of a high pressure cylinder through the pressure chamber in 300–600 ms. The pressure chamber has an exhaust, the diameter of which is made much smaller than the feedline. The pressure is built up by accumulation at this exhaust. If the pressure chamber were not previously filled with ethanol in the way described, the specimen would freeze before it were subjected to pressure. Ethanol in the pressure chamber is necessary for the correct correlation of the pressure build-up and cooling. It is disadvantageous in this respect that it possible for the ethanol to diffuse into the specimen and form artefacts in it or damage it. What is more, when the above-described method is employed, suspensions are often blown out of the metal half-shells.

It is often possible to achieve reproducible results by the half-shells, provided with the biological specimen, being immersed in 1-hexadecene. 1-hexadecene typically has the following advantages over aqueous solutions: no ice crystals can generally form outside the specimen; the low surface tension avoids gas bubbles, which would collapse during the pressure build-up, between the half-shells. Since 1-hexadecene is not water-miscible, the aqueous specimen is not changed during preparation. The freezing point is 4° C., but increases under pressure (2000 atm) to about 25° C., whereby a solid, but not rigid "shell" forms around the aqueous specimen. This "shell" is important in order not to lose the specimens during the cooling process under high pressure, since the nitrogen flow has a velocity of over 40 m/s (See, for example, STUDER D., MICHEL M. and MÜLLER M. High-pressure freezing comes of age, Scanning Microscopy Supplement 3, Vol. 189, pages 253–269).

However, biological specimens in the form of suspensions are still often difficult to handle with the technique using 1-hexadecene. Therefore, for receiving the biological specimens, preferably cellulose capillaries of about 200 $\mu$m inside diameter and 10 to 15 $\mu$m wall thickness of the porous wall have been used, cut into pieces of about 2 mm in length, placed between the metal half-shells and lightly clamped in place. These cellulose capillaries are surrounded by 1-hexadecene in the specimen holder. As already described, the specimens are frozen in a pressure chamber according to the prior art and, after freezing, may be manually removed from the thin-walled, metal half-shells, which serve as specimen holders (See, for example, H. HOHENBERG, K. MANNWEILER, M. MÜLLER, High-pressure freezing of cell suspensions in cellulose capillary tubes, Journal of Microscopy 175 (1294), 34–43, in particular FIG. 1, page 35).

The disadvantage of such specimen holders comprising metal half-shells is that the manipulation of the frozen specimens, in particular their removal from the solid 1-hexadecene, is difficult and often leads to specimens being damaged or lost. In addition, on account of their geometry, they are typically not suitable for the use of a separate circuit for the pressure transfer fluid, which in terms of apparatus is a more simple and therefore less costly means of transferring pressure to the specimen, as is described, for example, in DE-B 1 806 741.

SUMMARY OF THE INVENTION

An object of the present invention was accordingly to design specimen holders for receiving hydrous specimens, in particular in capillaries preferably made of cellulose or other materials. It was also an object to provide specimen holders which are generally suitable for use in high-pressure freezing apparatuses with separate circuits for the pressure transfer medium and coolant and to ensure easy and reliable manipulation of the frozen specimens, in particular during their removal from the specimen holder.

In accordance with these and other objectives, there is provided a specimen holder for a hydrous specimen comprising: (a) an inner hollow cylinder of a heat conductive material, (b) an inner hollow cylinder of a material which can be cut, (c) a cylindrical interior space within the inner hollow cylinder for receiving the specimen, and (d) the space between the inner hollow cylinder and an inside wall of the outer hollow cylinder being filled by a layer which is liquid at room temperature.

In yet further accordance with these and other objects, there is provided a method for freezing hydrous specimens under high pressure using a specimen holder, said method comprising: (a) introducing the hydrous specimen into a first hollow cylinder, (b) filling the cylindrical interior space of a second hollow cylinder with a substance which is liquid at room temperature, (c) manually introducing the first hollow cylinder into the interior space of the second hollow cylinder, (d) connecting the second hollow cylinder to corresponding receiving devices of a pressure transfer circuit of a high-pressure freezing system, (e) subjecting the specimen to high pressure for a short time, (f) intensely cooling the specimen for a short time so as to thereby freeze said specimen, (g) subjecting the specimen to atmospheric pressure, (h) bringing the specimen to a temperature at which the said substance melts, (i) pushing the specimen out of the second hollow cylinder by introducing an appropriately dimensioned instrument at the end of the second hollow cylinder, and (j) sending the specimen to further processing if desired.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

Preferred embodiments of the specimen holders according to the invention and their use are described below by way of example with reference to drawings, in which:

FIG. 1-B shows an enlarged cross section of a specimen holder according to B—B in FIG. 1-A;

FIG. 1-C shows an enlarged detail according to cutout C in FIG. 1-A;

FIG. 2-B shows a cross section of a specimen holder according to B—B in FIG. 2-A;

FIG. 2-C shows an enlarged detail according to cutout C in FIG. 2-A;

FIG. 3-B shows a cross section of a specimen holder according to B—B in FIG. 3-A;

FIG. 3-C shows an enlarged detail according to cutout C in FIG. 3-A;

FIG. 4-A shows a diagrammatic cross section through a cooling chamber of a high-pressure freezing apparatus with a specimen holding means fitted therein for cylindrical, thin specimens FIG. 4-B shows an enlarged detail according to cutout B in FIG. 4-A.

DETAILED DESCRIPTION OF A PREFERRED EMBODIMENT

Figure 1A:
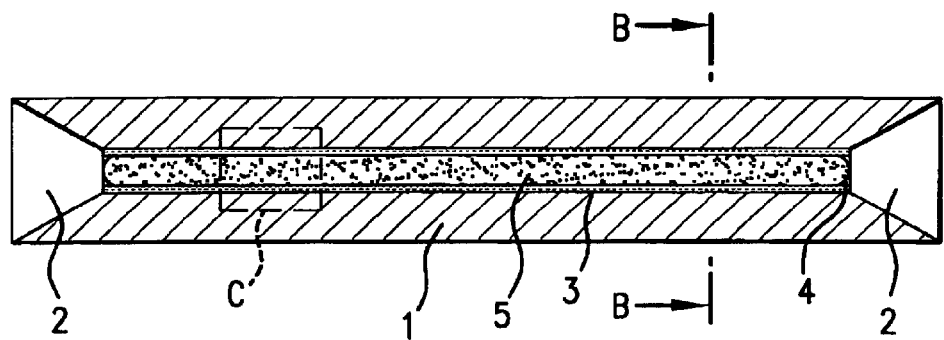
FIG. 1-A shows a longitudinal section of a specimen holder which comprises a solid heat conductive metal tube.

For purposes of the present invention, it is desirable to obtain specimen holders which generally have at least one of the following characteristics:

(–) transfer high cooling rates to the specimen, (–) permit rapid freezing under high pressure without the risk of accidents to the operating personnel, (–) can be provided with the capillaries made of cellulose or other materials in a relatively simple way, (–) permit easy and reliable manipulation of the frozen specimen, especially during removal of the capillaries from the specimen holder.

The specimen holder according to the invention substantially overcomes disadvantages associated with frozen specimens which cannot be further processed very easily. The present invention makes it possible for the frozen specimens to be sent in a simple and reliable way to many, if not all, known further processing methods, such as freeze etching, freeze drying, freeze substitution, freeze cutting etc.

The specimen holder according to the present invention is typically suitable for use in apparatuses which have a separate circuit for the pressure transfer medium and coolant, such as apparatuses, for example, described in German Patent DE-B 1 806 741. This permits use in relatively small, low-cost apparatuses for high-pressure freezing. As a result, the operational risk of high-pressure freezing is reduced considerably, since these small apparatuses typically employ a pressure transfer medium volume of less than 1 ml, while apparatuses which use liquid nitrogen both as a pressure transfer medium and as a coolant, according to the prior art, require at least 100 ml of pressure transfer medium. Using the specimen holders according to the present invention in apparatuses with a separate circuit for the pressure transfer medium and coolant, about one hundred times less pressure medium would be released in the event of an accident than in the apparatuses with liquid nitrogen as the pressure transfer medium and coolant. Thus, contrary to devices of the prior art, if there would be an accident, the amount of pressure medium would only cause very minimal damage.

The specimen holders according to the invention generally meet the precondition for freezing specimens under high pressure so that the same can be successfully used for light and electron microscopy in medicine and biology. The broad spectrum of specimens which can be frozen under high pressure at low cost with the specimen holders according to the present invention should further increase significantly the possibilities for the application of the high-pressure freezing method in the natural sciences (such as the description of ultrastructures). The high-pressure freezing of relatively thick specimens appears to be particularly advantageous for applications in pathology, since it is possible with the present specimen holder to provide thicker specimens to prepare good-quality histological sections for diagnosis in an extremely short time, for instance while an operation is in progress.

The specimen holder for hydrous specimens is preferably suitable for the high-pressure freezing of biological specimens, in particular microbiopsy specimens. In a preferred embodiment, it has a metal capillary with good heat conducting properties, i.e., a heat conductive metal, which is provided at each of both its end faces with a recess for receiving the connections for a pressure transfer medium. A sheathing in the form of a hollow cylinder preferably surrounds this capillary; in a preferred embodiment, it has a slit in its central section transverse to the principal axis and, in the axial direction, a bore for receiving the capillary. The sheathing allows reliable manipulation of the specimen holder, substantially prevents buckling of the thin metal capillaries during clamping in the high-pressure freezing system and allows the specimens to be removed from the apparatus without any problem after completion of the freezing cycle.

During the high-pressure freezing, in the interior of the metal capillary there is provided a hydrous, thin specimen which, according to a preferred embodiment, has been introduced into a capillary preferably made of a porous polymer material, most preferably of cellulose. After immersion in a substance which is liquid at room temperature, and is preferably not water-miscible (generally a hydrocarbon, for example, 1-pentene, 1-chlorobutane, etc.) and preferably has a low freezing point ($<-120°$ C.), the cellulose capillary is introduced into the metal capillary. As a result, a thin layer of the substance is formed between the cellulose capillary and the metal capillary.

Figure 1B:
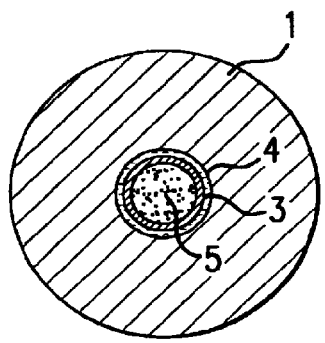
Figure 1C:
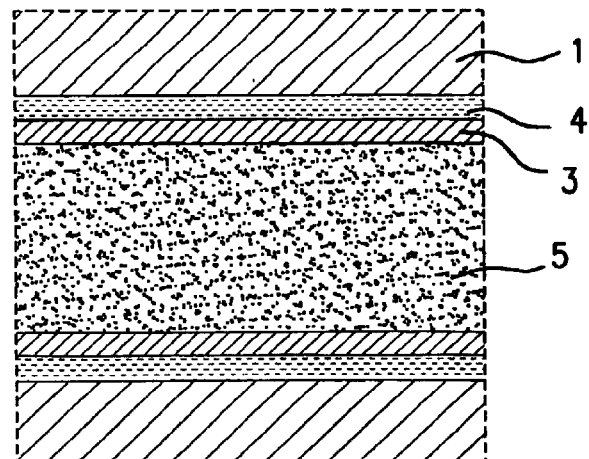

The specimen holder according to FIG. 1 has a solid metal tube 1 with good heat conducting properties (preferably made of copper, inside diameter preferably in the millimeter range, wall thickness corresponding to the inside diameter, length according to requirements in the range between about 10 and 20 mm). This tube 1 has at both end faces a recess 2, which may be shaped, for example, in the form of a cone and serves for receiving the connections for the pressure transfer medium. Fitted in this tube 1 is a very thin-walled second tube 3 made of a material with relatively good heat conducting properties, preferably a suitable polymer, the length of which preferably corresponds to the length of the tube 1 and which may be cut by means of the tools customary for the further processing of specimens. The polymer tube and metal tube are separated by a very thin layer 4 of a substance which is liquid at room temperature, and is preferably not water-miscible, most preferably a hydrocarbon (for example 1-pentene, 1-chlorobutane, etc.), which substance has a very low freezing point ($<-120°$ C.). In use, a relatively "thick", hydrous specimen 5 is introduced into the small tube 3, the latter subsequently being immersed in the fluid, e.g. the hydrocarbon 4, and pushed into the tube 1. Excess hydrocarbon escapes on the opposite side of the tube 1 and can be manually wiped away there. During the process of high-pressure freezing, the specimen 5 is located in the small polymer tube 3.

Figure 2A:
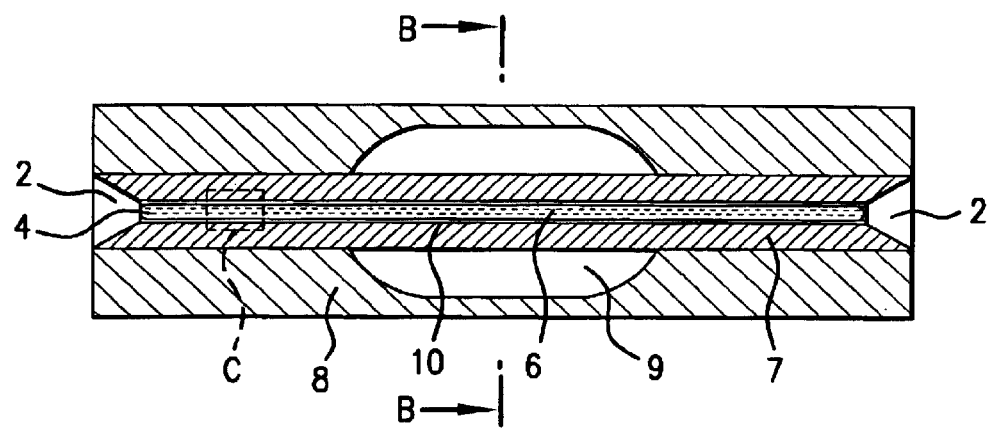
FIG. 2-A shows a longitudinal section of a specimen holder for cylindrical, thin specimens with an inside diameter in the range of about 0.3 mm.
Figure 2B:
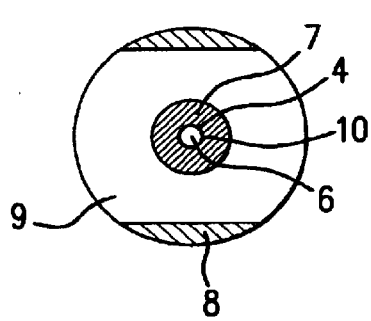
Figure 2C:
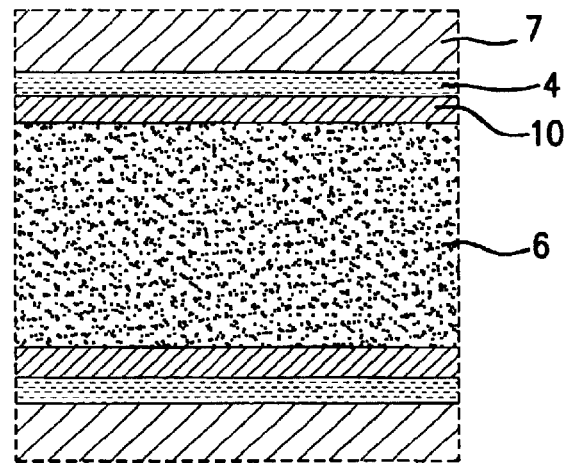

The specimen holder according to FIG. 2 is suitable for cylindrical "thin" specimens 6 of a diameter preferably in the range of max. about 0.3 mm. It has a metal capillary 7 with good heat conducting properties, which in a preferred embodiment consists of copper and has a preferred inside diameter in the range between 0.1 and 0.5 mm, preferably of 0.3 mm, and a preferred wall thickness in the range from 0.3 to 0.3 mm. This capillary 7 is provided at each of both end faces with a recess, preferably an inner cone 2, for receiving the connections of lines, for example, for a pressure transfer medium (high-pressure lines). A sheathing 8 in the form of a hollow cylinder preferably surrounds this capillary 7 and represents an integral part of the specimen holder. It is preferably produced from stainless steel and has in its middle part a recess in the form of a slit 9 transversely to the principal axis and, in the axial direction, a bore of a diameter corresponding to the outside diameter of the capillary 7. The capillary 7 is generally pressed in a form-fitting manner into its sheathing 8. This sheathing 8 allows simple manipulation of these specimen holders, prevents buckling of the relatively thin metal capillaries during clamping into the high-pressure freezing system. The present arrangement also generally allows the specimens to be removed without any problem from the apparatus after completion of the freezing cycle, since jamming by deformed capillary ends is reliably and substantially prevented.

During the high-pressure freezing, in the interior of the metal capillary 7 there is a hydrous, thin specimen 6, which has been introduced into a capillary 10, preferably made of a porous polymer material. The polymer material is intended on the one hand to be porous and on the other hand to be able to be cut by means of the tools customary for the further processing of biological specimens. For example, capillaries made of porous cellulose, as are used in blood dialysis units, satisfy both these criteria. In a preferred embodiment, such a capillary 10 has an inside diameter in the range from 0.1 to 0.5 mm and a wall thickness in the range from 0.01 to 0.1 mm. After immersion in a fluid 4 which is liquid at room temperature and preferably not water-miscible, most preferably a hydrocarbon or a halogenated hydrocarbon (for example 1-pentene, 1-chlorobutane, etc.), which has a low freezing point ($<-120°$ C.), the capillary 10 made of the porous material is introduced into the metal capillary 7. As a result, the capillary 10 made of the porous material and the metal capillary 7 are separated from each other by a thin layer of the substance 4, preferably a hydrocarbon.

The capillaries preferably made of cellulose preferably originate, for example, from blood dialysis units. They can be used in polyvalent applications and permit the high-pressure freezing of small organisms (for example Nematoda), Protista, microorganisms, but also tissue microbiopses (brain, liver, etc.) as well as gels, suspensions, etc.

Figure 3A:
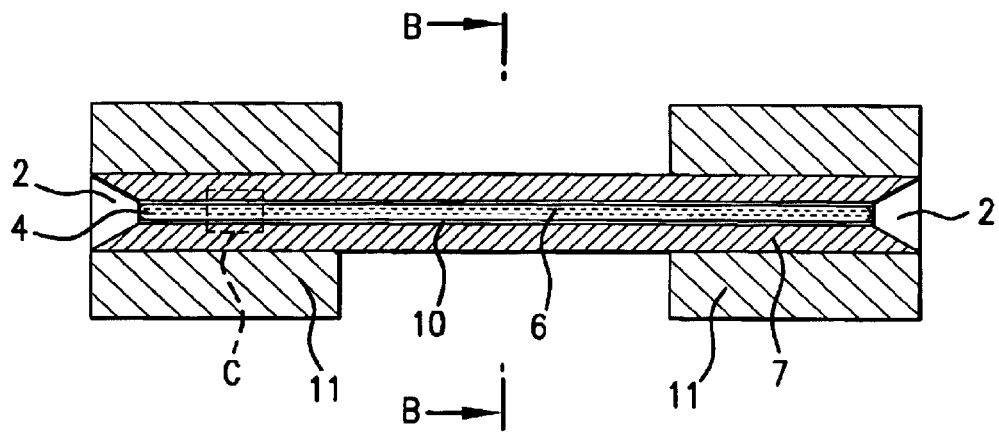
FIG. 3-A shows a longitudinal section of a specimen holder for cylindrical, thin specimens with an inside diameter in the range of 0.3 mm.
Figure 3B:
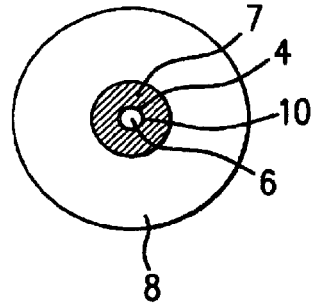
Figure 3C:
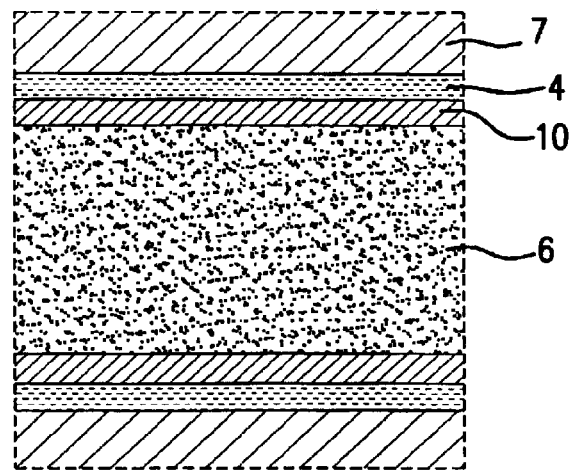

The specimen holder according to FIG. 3 is likewise suitable for cylindrical, relatively thin specimens 6 of a diameter in the range of max. 0.3 mm and comprises a metal capillary 7 with good heat conducting properties (preferably made of copper), which is provided at each of its end faces with a recess 2, for example in the form of a cone, for receiving the connections for the pressure transfer medium.

As distinct from the specimen holder from FIG. 2, the capillary 7 is sheathed at both its ends with a hollow cylinder 11, preferably made of stainless steel, which represent an integral part of the specimen holder and the hollow cylinders 11 preferably can be manipulated together with the holder. The difference with respect to the sheathing 8 from FIG. 2 is that the cooling of the specimen is generally more efficient, but the specimen holder as a whole can be less stable. The hydrous specimen 6 inside the metal capillary 7 has been introduced into a capillary 10 of the type described, made of a porous polymer material. The metal capillary and the capillary made of the porous material are separated in the same way as described for the specimen holders from FIGS. 1 and 2 by a layer of a substance 4 which is liquid at room temperature and generally not water-miscible, preferably a hydrocarbon or halogenated hydrocarbon (for example 1-pentene, 1-chlorobutane, etc.), which has a very low freezing point (<−120° C.) and ensures optimum heat conduction between specimen 6 and metal capillary 7.

The method of using the specimen holders according to the invention for the purpose of high-pressure freezing of hydrous specimens has the following preferred method steps. For the relatively "thick" specimens of FIG. 1, the same method is used; however, the manipulations can be carried out more easily, since the dimensions are larger.

The hydrous specimens 6, preferably made of biological material, are introduced into the porous capillaries 10 and the metal capillary 7 as follows: the capillaries 10, preferably made of porous cellose, are generally bonded by a suitable adhesive in a way known per se in pipette tips made of plastic (tips of so-called Eppendorf® micropipettes). By fitting these tips onto a micropipette of a corresponding size, the specimen is introduced into the porous capillary 10, either by utilizing the capillary forces or by slight suction, while observing through a stereo magnifying glass. In the case of the biopsy needles often used today, before being sucked up, the tissue prepared for microbiopsy should be slit lengthwise by means of a razor blade or some other suitable instrument.

While observing through a stereo magnifying glass, the specimen holders are placed in a Petri dish filled with fluid 4, preferably a hydrocarbon or halogenated hydrocarbon which is not water-miscible and has a low melting point, whereby the metal capillaries 7 fill up with the fluid. A filter paper lying on the bottom of the Petri dish, if needed, serves for removing excess specimen fluid on the surface of the capillary 10 of a porous material, filled with the specimen 6. The capillary 10, freed in this way of excess specimen fluid, is manually introduced into the metal capillaries 7 with the aid of two tweezers or other suitable instruments. The length of the porous capillary 10 should in this case correspond approximately to the length of the metal capillary 7. This is important, since only that region of the specimen 6 in the porous capillary 10 which is in the region of the metal capillary 7 not sheathed by the sheathing 8 or 11 is frozen well by the freezing cycle. Providing the specimen holders with the specimen 6 should take only just a few seconds, in order to minimize outside influences on the specimen 6. The specimen holders provided with the specimens are freezed immediately.

The method of freezing the specimen holders according to the invention under high pressure is explained in FIG. 4 on the basis of a specimen holder 12 according to FIG. 3, but also applies analogously to the specimen holders which are represented in FIGS. 1 and 2. In FIG. 4, the specimen holder 12 is fitted into a specimen holder receptacle 13 of a design known per se and is securely clamped by means of an O-ring 14. Subsequently, the filled specimen holder receptacle 13 is introduced into the centered bores 15 provided for this purpose in a high-pressure freezing system. The two sheathings 11 of the specimen holder 12 thereby fit into the centered bores 15. The central portion of the specimen holder 12, corresponding to the unsheathed part of the metal capillary 7, lies in a cavity 16, which is formed by a slit of the cylindrical guide 17. This is necessary in order to allow the greatest possible volumes of the coolant (K) per unit of time to impinge on the specimen holder 12.

The specimen holder is subsequently connected to the circuit of the pressure transfer medium: the metal capillary 7 of the specimen holder 12 is pressed at its one end onto the conical opening of a high-pressure line 20 by means of a solid cone 18, with a specific force (F) which is generated, for example, by a compressed-air cylinder 19. The specimen 6 is consequently connected in a sealed manner by the specimen holder 12, clamped in place in this way, to the high-pressure system, i.e. the conically tapered high-pressure line 20, and is fixed in the bores 15. The high-pressure line 20 filled with a pressure transfer medium, for example, hydraulic oil 21, which line is connected to a pressure generator 22, subjects the specimen 6 to the chosen high pressure at the desired point in time and said specimen is subsequently frozen.

The coolant is briefly deflected onto the metal capillary 7 via a solid feeding means (not shown), which completely surrounds the cavity 16. By mechanical coupling of the coolant deflection and the release of the arresting of the ram 23, pressure values in the range between 1000 and 3000 bar, preferably in a range between 1600 and 2045 bar, are achieved in the specimen 6 within a time period in the range from 0.10 to 50 msec, preferably less than 20 msec, for example around 10 msec. Synchronously with this, a cooling in the range between 50 (fifty) and $10^6$ (1 million) ° K./sec, preferably of several 1000° K./sec, is achieved at the surface of the metal capillary 7. As a result, a temperature in the range between −90 and −196° C. is obtained in the specimen 6, whereby the latter is frozen. The relatively "thick" specimens represented in FIG. 1 may expediently also be frozen at lower cooling rates (less than 5000° K./sec). For cooling, a commercially available coolant, preferably a hydrocarbon with a low boiling point, for example, propane, can be used, which coolant can be stored in a metal tank which is precooled from outside with liquid nitrogen to a temperature of about −180° C.

Directly after freezing the specimen 6, the compressed-air piston 24 of the compressed-air cylinder 19 is drawn back and the specimen 6 in the specimen holder 12 is removed from the high-pressure freezing system with the aid of the handle 25 on the specimen holder receptacle 13 and is immediately immersed in liquid nitrogen at atmospheric pressure. Under liquid nitrogen, the specimen holder 12 is manually removed from the specimen holder receptacle 13 with the aid of tweezers. The specimen holder 12 is kept in liquid nitrogen until further processing of the specimen 6.

The now frozen specimen 6 is removed as follows from the specimen holder 12: under liquid nitrogen, the specimen holder 12 is introduced into a cryostat. At the temperature of the cryostat (in the range generally from −90 to −140° C., for example −120° C.), the hydrocarbon or other substance 4 (for example 1-pentene with a melting point of −165° C.), which is surrounding the cellulose capillary 10, melts. As a result, the frozen capillaries 10 made of the porous polymer material can be manually pushed out of the metal hollow cylinder 7 with the aid of a cooled cylinder (in the range around −120° C.), preferably a metal instrument, for example, a drill of a corresponding diameter, while observing through a stereo magnifying glass. The capillary 10 with the specimen 6, removed in such a way, can in turn be stored in liquid nitrogen or be further processed. Subsequently, the specimen 6 in the capillaries 10 can be expediently sent for further processing by one of the methods known per se. The capillary 10 made of the porous polymer material, preferably porous cellulose, does not hinder this, in particular does not hinder the cutting of the specimen.

The same applies to the manipulation of the relatively "thick" specimens 5. The thin-walled small polymer tube 3 of the specimen holder from FIG. 1 likewise allows any type of further processing.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

The Priority Document, Swiss Patent Application 0053/97, filed Jan. 13, 1997 is incorporated herein in its entirety by reference. In addition, all documents and references referred to herein are specifically incorporated by reference.

For the purposes of the following claims, the terms "the", "a" and "an" are intended as refering to singular or plurals.

What is claimed is:

1. A specimen holder for a hydrous specimen for high-pressure freezing comprising:
   (a) an outer hollow cylinder,
   (b) an inner hollow cylinder of a material which can be cut, wherein the inner hollow cylinder is a capillary, wherein the outer hollow cylinder is of a metal material
   (c) a cylindrical interior space within said inner hollow cylinder for receiving said specimen, and
   d) a space between the inner hollow cylinder and an inside wall of the outer hollow cylinder for being filled by a layer which is liquid at room temperature whereby the inner hollow cylinder is separable from and is capable of being manually pushed out of the outer hollow cylinder when the layer which is liquid at room temperature is thawed,
   wherein the inner hollow cylinder is a capillary comprising a porous polymer material, and
   wherein the space between the inner hollow cylinder and the inside wall of the outer hollow cylinder is filled with the layer which is a liquid at room temperature, and the layer which is a liquid at room temperature is of a hydrocarbon material.

2. A specimen holder as claimed in claim 1, wherein the outer hollow cylinder includes two end faces, each of which include a recess capable of accommodating connecting lines.

3. A specimen holder as claimed in claim 1, wherein said holder further comprises a sheathing and has the form of a hollow cylinder, said sheathing being provided with a bore in an axial direction thereof that is capable of receiving said outer hollow cylinder.

4. A specimen holder for a hydrous specimen for high-pressure freezing comprising:
   (a) an outer hollow cylinder,
   (b) an inner hollow cylinder of a material which can be cut, wherein the inner hollow cylinder is a capillary, wherein the outer hollow cylinder is of a metal material
   (c) a cylindrical interior space within said inner hollow cylinder for receiving said specimen, and
   (d) a space between the inner hollow cylinder and an inside wall of the outer hollow cylinder for being filled by a layer which is liquid at room temperature whereby the inner hollow cylinder is separable from and is capable of being manually pushed out of the outer hollow cylinder when the layer which is liquid at room temperature is thawed,
   wherein the outer hollow cylinder includes two end faces, each of which include a recess capable of accomodating connecting lines, and
   wherein said end faces both comprise hollow cylinders, said cylinders being capable of receiving said outer hollow cylinder but do not enclose said outer hollow cylinder over its entire length, and
   wherein the space between the inner hollow cylinder and the inside wall of the outer hollow cylinder is filled with the layer which is a liquid at room temperature, and the layer which is a liquid at room temperature is of a hydrocarbon material.

5. A specimen holder as claimed in claim 1, wherein said layer in said space comprises a water insoluble substance.

6. A specimen holder for a hydrous specimen for high-pressure freezing comprising:
   (a) an outer hollow cylinder,
   (b) an inner hollow cylinder of a material which can be cut, wherein the inner hollow cylinder is a capillary, wherein the outer hollow cylinder is of a metal material
   (c) a cylindrical interior space within said inner hollow cylinder for receiving said specimen, and
   (d) a space between the inner hollow cylinder and an inside wall of the outer hollow cylinder for being filled by a layer which is liquid at room temperature whereby the inner hollow cylinder is separable from and is capable of being manually pushed out of the outer hollow cylinder when the layer which is liquid at room temperature is thawed,
   wherein the inner hollow cylinder comprises a porous polymer material and has an inside diameter in the range from 0.1 to 0.5 mm and a wall thickness in the range from 0.01 to 0.1 mm, and
   wherein the space between the inner hollow cylinder and the inside wall of the outer hollow cylinder is filled with the layer which is a liquid at room temperature, and the layer which is a liquid at room temperature is of a hydrocarbon material.

7. A specimen holder as claimed in claim 1, wherein the specimen holder is at a temperature at which the layer is frozen.

8. A specimen holder as claimed in claim 4, wherein the specimen holder is at a temperature at which the layer is frozen.

9. A specimen holder as claimed in claim 4, wherein said layer in said space comprises a water insoluble substance.

10. A specimen holder as claimed in claim 6, wherein the specimen holder is at a temperature at which the layer is frozen.

11. A specimen holder as claimed in claim 6, wherein layer in said space comprises a water insoluble substance.

* * * * *